United States Patent [19]
Gebhard et al.

[11] Patent Number: 5,620,966
[45] Date of Patent: Apr. 15, 1997

[54] 11,21-BISPHENYL-19-NORPREGNANE DERIVATIVES

[75] Inventors: Ronald Gebhard, Oss; Hendrikus A. A. van der Voort, Veghel, both of Netherlands

[73] Assignee: Akzo Nobel N.V., Arnhem, Netherlands

[21] Appl. No.: 445,119

[22] Filed: May 19, 1995

[30] Foreign Application Priority Data

May 19, 1994 [EP] European Pat. Off. ............. 94201431

[51] Int. Cl.$^6$ ............................ A61K 31/565; C07J 1/00
[52] U.S. Cl. ...................... 514/174; 514/176; 514/179; 514/182; 540/106; 540/107; 540/109; 540/116; 552/520; 552/648
[58] Field of Search ........................ 552/520, 648; 514/182, 174, 176, 179; 540/106, 107, 109, 116

[56] References Cited

U.S. PATENT DOCUMENTS

| | | | |
|---|---|---|---|
| 4,386,085 | 5/1983 | Teutsch et al. | 424/238 |
| 4,447,424 | 5/1984 | Teutsch et al. | 424/238 |
| 4,477,445 | 10/1984 | Philibeit et al. | 424/239 |
| 4,519,946 | 5/1985 | Teutsch et al. | 514/179 |
| 4,536,401 | 8/1985 | Neef et al. | 514/173 |
| 4,540,686 | 9/1985 | Philibeit et al. | 514/179 |
| 4,547,493 | 10/1985 | Teutsch et al. | 514/179 |
| 4,609,651 | 9/1986 | Rohde et al. | 514/179 |
| 4,634,695 | 1/1987 | Torelli et al. | 514/178 |
| 4,634,696 | 1/1987 | Teutsch et al. | 514/179 |
| 4,661,295 | 4/1987 | Joquey et al. | 260/397.45 |
| 4,771,042 | 9/1988 | Braughler et al. | 514/171 |
| 4,774,236 | 9/1988 | Cook et al. | 514/176 |
| 4,780,461 | 10/1988 | Reef et al. | 514/179 |
| 4,814,327 | 3/1989 | Ottow et al. | 514/179 |
| 4,829,060 | 5/1989 | Ottow et al. | 514/179 |
| 4,891,365 | 1/1990 | Wiechert et al. | 514/173 |
| 4,921,845 | 5/1990 | de Jongh et al. | 514/172 |
| 4,954,490 | 9/1990 | Cook et al. | 514/176 |
| 5,006,518 | 4/1991 | Moguilewsky et al. | 514/179 |
| 5,064,822 | 11/1991 | Philibert et al. | 514/179 |
| 5,073,548 | 12/1991 | Cook et al. | 514/169 |
| 5,108,996 | 4/1992 | Claussner et al. | 514/176 |
| 5,149,696 | 9/1992 | Claussner et al. | 514/179 |
| 5,162,312 | 11/1992 | Kash et al. | 514/179 |
| 5,173,483 | 12/1992 | Grandadam | 514/178 |
| 5,244,886 | 9/1993 | Scholz et al. | 514/175 |
| 5,273,971 | 12/1993 | Scholz et al. | 514/176 |
| 5,276,023 | 1/1994 | Maguilewsky et al. | 514/179 |
| 5,290,771 | 3/1994 | Claussnner et al. | 514/172 |
| 5,407,928 | 4/1995 | Kasch et al. | 514/179 |
| 5,446,036 | 8/1995 | Scholz et al. | 514/175 |

FOREIGN PATENT DOCUMENTS

| | | |
|---|---|---|
| 0057115 | 8/1982 | European Pat. Off. . |
| 0245170 | 11/1987 | European Pat. Off. . |
| 9504536 | 2/1995 | WIPO ............... A61K 31/57 |

*Primary Examiner*—Kimberly J. Prior
*Attorney, Agent, or Firm*—William M. Blackstone

[57] ABSTRACT

The invention relates to a 11,21-bisphenyl-19-norpregnane derivative of formula I

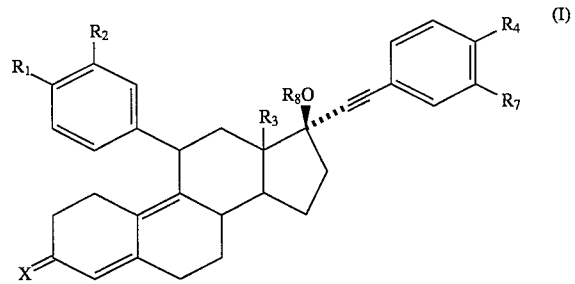

wherein $R_1$ is selected from H, halogen, (1–6C)alkoxy, and $NR_5R_6$, $R_5$ and $R_6$ being independently hydrogen or (1–6C)alkyl or $R_5$ and $R_6$ together are (3–6C)alkylene; $R_2$ is hydrogen; or $R_1$ and $R_2$ together are a (1–3C)alkylenedioxy group, optionally substituted by one or more halogen atoms; $R_3$ is methyl or ethyl; $R_4$ is selected from C(O)-$NR_5R_6$, $SO_n$-(1–6C)alkyl optionally substituted by one or more halogen atoms, $SO_n$-(3–6C)cycloalkyl, n being 1 or 2, $SO_2$-$NR_5R_6$, 2-oxypyrrolidinyl, and $NR_5R_6$; $R_7$ is H or (1–6C)alkyl; $R_8$ is H or carboxy-1-oxo(1–6C)alkyl; and X is selected from (H,OH), O, and NOH; 11 or a pharmaceutically acceptable salt thereof.

The compounds of the invention have anti-glucocorticoid activity and can be used in treating or preventing glucocorticoid-dependent diseases.

8 Claims, No Drawings

11,21-BISPHENYL-19-NORPREGNANE DERIVATIVES

The invention relates to a 11,21-bisphenyl-19-norpregnane derivative, a process for the preparation thereof, a pharmaceutical composition containing the same, as well as the use of said derivative for the manufacture of a medicament.

Various 11,21-bisphenyl-19-norpregnane derivatives are known. In U.S. Pat. No. 4,447,424, for example, a 11β-[4-(N,N-dimethylamino)-phenyl]-21-phenyl-19-norpregnane derivative is disclosed. The class of steroids described in this patent may carry a variety of substituents at the 11- and 17-position, respectively. The compounds show anti-glucocorticoid activity. At the same time, they show anti-progesterone activity, which is also a property of the 11-(alkynyl substituted) phenyl-21-phenyl-19-norpregnane derivatives disclosed in EP 245,170. This is a serious drawback since the anti-progesterone property (like anti-implantation and abortive activities) restricts the therapeutic potential in the treatment of glucocorticoid dependent diseases, like Cushing syndrome, diabetes, glaucoma, depression, arteriosclerosis, adiposity, hypertension, sleep disturbances and osteoporosis. Therefore, in this field currently searches are done which should lead to new compounds having selective anti-glucocorticoid activity. Until now, however, the search for such compounds has only been partially successful. Although compounds were prepared with a more selective anti-glucocorticoid activity-profile in vitro, these compounds lack in vivo anti-glucocorticoid activity (see D. Philibert et al. in Agarwal MK (ed): Antihormones in Health and Disease. Front Horm. Res. Basel, Karger, 1991, vol 19, pp 1–17). Surprisingly, it has now been found that 11,21-bis-phenyl-19-norpregnane derivatives of formula I

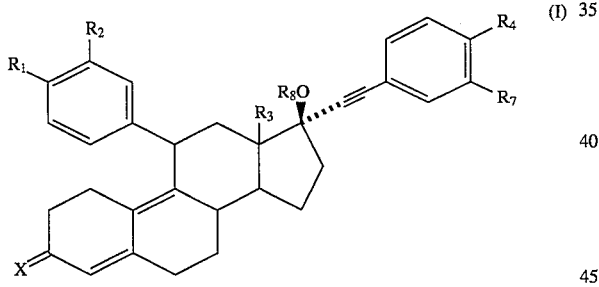

wherein $R_1$ is selected from H, halogen, (1–6C)alkoxy, and $NR_5R_6$, $R_5$ and $R_6$ being independently hydrogen or (1–6C)alkyl or $R_5$ and $R_6$ together are (3–6C)alkylene; $R_2$ is hydrogen; or $R_1$ and $R_2$ together are a (1–3C)alkylenedioxy group, optionally substituted by one or more halogen atoms; $R_3$ is methyl or ethyl; $R_4$ is selected from C(O)-$NR_5R_6$, $SO_n$-(1–6C)alkyl optionally substituted by one or more halogen atoms, $SO_n$-(3–6C)cycloalkyl, n being 1 or 2, $SO_2$—$NR_5R_6$, 2-oxypyrrolidinyl, and $NR_5R_6$; $R_7$ is H or (1–6C)alkyl; $R_8$ is H or carboxy-1-oxo(1–6C)alkyl; and X is selected from (H,OH), O, and NOH; or a pharmaceutically acceptable salt thereof, show both in vitro selectivity and in vivo anti-glucocorticoid activity or are metabolized in the body into compounds having these properties. These 11,21-bisphenyl-19-norpregnane derivatives form a new class of compounds having a selective affinity to glucocorticoid receptors and in vivo anti-glucocorticoid activity.

Preferred compounds according to this invention are 11,21-bisphenyl-19-norpregnane derivatives wherein $R_3$ is methyl and $R_4$ is selected from $SO_2$-(1–6C)alkyl optionally substituted by one or more fluorine atoms, $SO_2$-(3–6C)cycloalkyl, and $NR_5R_6$. Especially mentioned are derivatives wherein $R_4$ is $N(CH_3)_2$ or $SO_2CH_3$. Particularly useful are derivatives wherein $R_4$ is $SO_2CH_3$. Other preferred compounds are 11,21-bisphenyl-19-norpregnane derivatives wherein $R_1$ is $NR_5R_6$ and $R_2$ is hydrogen; or $R_1$ and $R_2$ together form a (1–3C)alkylenedioxy group. More preferred are derivatives wherein $R_1$ is $N(CH_3)_2$, and $R_2$ is hydrogen; or $R_1$ and $R_2$ form together a methylenedioxy or an ethylenedioxy group.

The most preferred compound is the 11,21-bisphenyl-19norpregnane derivative (11β,17α)-11-[4-(dimethylamino)phenyl]-17-hydroxy-21-[4-(methylsulfonyl)phenyl]-19-norpregna-4,9-dien-20-yn-3-one.

The term halogen means a fluorine, chlorine, bromine or iodine atom. Fluorine is the preferred halogen. The term (1–6C)alkyl used in the definitions of $R_5$, $R_6$ and $R_7$ means an alkyl group having 1–6 carbon atoms, for example methyl, ethyl, propyl, isopropyl, butyl, secbutyl, tert-butyl, pentyl, neopentyl and hexyl. The term (1–6C)alkoxy used in the definition of $R_1$ means an alkoxy group having 1–6 carbon atoms, the alkyl moiety having the meaning as previously defined. The term (1–3C)alkylene in the definitions of $R_1$ and $R_2$ means an alkylene group having 1–3 carbon atoms, for example methylene and ethylene. The term (3–6C)alkylene in the definitions of $R_5$ and $R_6$ means an alkylene group having 3–6 carbon atoms, for example butylene and pentylene. A preferred carboxy-1-oxo(1–6C)alkyl group is 3-carboxy-1-oxopropyl.

The 11,21-bisphenyl-19-norpregnane derivatives according to the present invention can be prepared by a process wherein a compound of formula II

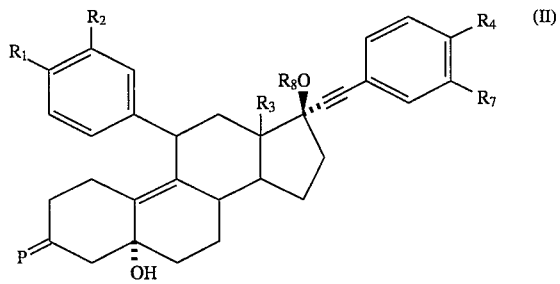

wherein P is a protected keto-group, is dehydrated and deprotected, and optionally converted into the corresponding 3-hydroxy- or 3-oxime derivative, after which the compound obtained is optionally converted into a pharmaceutically acceptable salt.

The derivatives of formula II may be prepared according to well known methods described and used for the preparation of steroids. A suitable process for the preparation of derivatives of formula II starts from estra-4,9-diene-3,17-dione or its 18-methyl derivative. Selective reduction of the 17-keto group to 17β-OH, 17α-H, e.g. with sodiumborohydride, followed by protection of the 3-keto group, e.g. by ketalisation with ethyleneglycol, triethylorthoformate and p-toluenesulfonic acid, and reoxidation of the 17-hydroxy group, e.g. with pyridinium chlorochromate, provides the 3-protected estra-5(10),9(11)-diene-3,17-dione or its 18-methyl analogue. Ethynylation at the 17-position (yielding a 17α-ethynyl,17β-OH derivative), followed by epoxidation of the 5(10) double bond, e.g. with hydrogen peroxide, trifluoroacetophenone, and pyridine in dichloromethane according to the method as disclosed in European patent application EP 0 298 020, provides the 3-protected 5α,10α-epoxy-17α-ethynyl-17β-hydroxy estr-9(11)-ene-3-one or its 18-methyl analogue. Subsequently, the epoxide can be substituted at its 11position with the group $R_1R_2C_6H_3$, wherein $R_1$ and $R_2$ have the previously defined meanings, for example by a Cu-catalyzed Grignard reaction. The resulting compound can be furnished at its 21-position with the group $R_4R_7C_6H_4$, wherein $R_4$ and $R_7$ have the previously defined meanings, for example by a Pd/Cu-catalyzed Heck-reaction (see R. F. Heck, Palladium Reagents in Organic Synthesis, Academic Press, 1985) in an appropriate secondary or tertiary amine, which leads to compounds of formula II.

Suitable protective groups and methods to remove these groups are known in the art, for example from T. W. Green: Protective Groups in Organic Synthesis (Wiley, N.Y., 1981). Particularly suitable protective groups for the protection of keto groups are acetals, e.g. 1,2-ethylene ketal.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methane-sulphonic acid, fumaric acid, succinic acid, tartaric acid, citric acid, benzoic acid, and ascorbic acid.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

In Tables I and II the receptor affinity of the compounds of the invention for glucocorticoid receptors (GR) related to progesterone receptors (PR) is presented in comparison with the GR/PR ratio for (11β,17α)-11-[4-(dimethylamino)phenyl]-17-hydroxy-21-phenyl-19-norpregna-4,9-dien-20-yn-3-one which is disclosed in U.S. Pat. No. 4,447,424.

The glucocorticoid affinity of the compounds was measured for glucocorticoid receptors present in intact human multiple myeloma cells and compared with the affinity of dexamethasone (according to the procedure described by H. J. Kloosterboer et al., J. Steroid Biochem., Vol. 31, 567–571 (1988)). The progesterone affinity of the compounds was measured for cytoplasmic progesterone receptors present in human breast tumor cells and compared with the affinity of (16α)-16-ethyl-21-hydroxy-19-norpreg-4-ene-3,20-dione (according to the procedure described by E. W. Bergink et al., J. Steroid Biochem., Vol. 19, 1563–1570 (1983)).

TABLE I

Compounds of formula I wherein $R_3$ is methyl and X is O:

| $R_1$ | $R_2$ | $R_4$ | GR/PR |
|---|---|---|---|
| $N(CH_3)_2$ prior art | H | H | 6 |
| $N(CH_3)_2$ | H | $N(CH_3)_2$ | 36 |
| $N(CH_3)_2$ | H | pyrrolidinyl (N-) | 64 |
| $N(CH_3)_2$ | H | 2-oxopyrrolidinyl (N-) | 43 |
| $N(CH_3)_2$ | H | $C(O)-NH_2$ | 12 |
| $N(CH_3)_2$ | H | $C(O)-N(CH_3)_2$ | 19 |
| $N(CH_3)_2$ | H | $C(O)-N$(pyrrolidinyl) | 28 |
| $N(CH_3)_2$ | H | $SOCH_3$ | 11 |
| $N(CH_3)_2$ | H | $SO_2CH_3$ | 53 |
| $N(CH_3)_2$ | H | $SO_2N(CH_3)_2$ | 26 |
| $N(CH_3)_2$ | H | $SO_2-N$(pyrrolidinyl) | 49 |
| $O-CH_2-O$ | $O-CH_2-O$ | $N(CH_3)_2$ | 11 |
| $O-CH_2-O$ | $O-CH_2-O$ | $SO_2CH_3$ | 255 |
| H | H | $N(CH_3)_2$ | 23 |
| H | H | $SO_2CH_3$ | 45 |

TABLE II

Compounds of formula I wherein $R_3$ is methyl and X is NOH:

| $R_1$ | $R_2$ | $R_4$ | GR/PR |
|---|---|---|---|
| $N(CH_3)_2$ E-isomer | H | $N(CH_3)_2$ | 15 |
| $N(CH_3)_2$ Z-isomer | H | $N(CH_3)_2$ | 24 |

From these Tables it can be concluded that the 11,21-bisphenyl-19-norpregnane derivatives of the invention show a greater selectivity for glucocorticoid receptors in comparison with the known 11,21-bisphenyl-19-norpregnane derivative (11β,17α)-11-[4-(dimethylamino)phenyl]-17-hydroxy-21-phenyl-19-norpregna-4,9-dien-20-yn-3-one.

The invention is further illustrated by the following examples.

Starting materials: Examples I–IV

EXAMPLE I

4-[(trifluoromethyl)sulfonyl]oxy-2-methyl-(methylsulfonyl)benzene a) A solution of 90 g of oxone dissolved in 1800 ml of water was added to a vigorously stirred solution of 15.43 g of 4-(methylthio)-m-cresol. The temperature was maintained below 15° C. and stirring was continued for 3 hours.

Work-up was accomplished by extraction with dichloromethane, followed by washing the organic layer with sodium thiosulfate and a saturated brine solution. Evaporation provided 18.4 g of 4-hydroxy-2-methyl(methylsulfonyl)benzene;

m.p. 105° C.

b) 7 g of 4-hydroxy-2-methyl-(methylsulfonyl)benzene were dissolved in 210 ml of dichloromethane and 14 ml of pyridine. After cooling of the mixture to 0°–5° C., a solution of 7.1 ml of triflic anhydride in 70 ml of dichloromethane was added in 30 minutes. Stirring was continued for 1 hour at room temperature. Work-up was accomplished by pouring the mixture onto ice-water and extracting with dichloromethane. Evaporation and purification with column chromatography (heptane/ethyl acetate 6/4) provided 9.9 g of 4-[(trifluoromethyl)sulfonyl]oxy-2-methyl-(methylsulfonyl)benzene;

m.p. 51° C.

EXAMPLE II

A 4-bromo-(ethylsulfonyl)benzene 6.25 ml of 2N NaOH (52.5 mmol) were added to a stirred suspension of 9.95 g (50 mmol) of 4-bromothiophenol in 50 ml of water. Stirring was continued for 30 min at room temperature and then 4.5 ml (56 mmol) of ethyliodide were added in 2 minutes. After 16 hours the mixture was poured into water and extracted with diethylether, followed by washing the organic layer with brine. Drying with $MgSO_4$ and evaporation provided 11 g of 4-bromophenylthioethylether.

According to the procedure described in example Ia), 10 g of the previously obtained compound were converted into 12.4 g of 4-bromo-(ethylsulfonyl)benzene; m.p. 53° C.

The following reagents have been prepared similarly from 4-bromo-thiophenol by reaction with the appropriate alkylhalide:

B 4-bromo-(isopropylsulfonyl)benzene; m.p. 63° C.

C 4-bromo-(cyclopentylsulfonyl)benzene; m.p. 76° C; (1H NMR, 200 Mhz, $CDCl_3$: 3.47 ppm, m, 1H).

EXAMPLE III

N-(4-bromophenyl)-2-pyrrolidinone 8.06 g of N-phenylpyrrolidinone were dissolved in 33 ml glacial acetic acid; the mixture was cooled to 0°–5° C. and then a solution of 2.65 ml bromine in 12 ml of glacial acetic acid was added dropwise. Stirring was continued for 30 minutes at room temperature. Work-up was accomplished by pouring the mixture into 1 l of water and neutralizing the mixture with KOH. The solid was filtered and dissolved in ethylacetate and washed with a sodium thiosulphate solution until the brown colour disappeared; washing with brine and drying with $MgSO_4$ provided 8.5 g of a white crystalline mass that could be recrystallized from ether; m.p. 102° C.

EXAMPLE IV

4-Bromo-N,N-dimethylsulfonamide

According to the general method described in J. Am. Chem. Soc. 45, 2697 (1923) the following reagents were prepared from 4-bromophenylsulfonylchloride:

A 4-bromophenylsulfonamide: m.p. 167° C.

B 4-bromophenyl-N-methylsulfonamide: m.p.: 77° C.

C 4-bromophenyl-N,N-dimethylsulfonamide: m.p. 93° C.

D N-(4-bromophenylsulfonyl)-pyrrolidine: m.p. 95° C.

Starting with 4-bromophenylbenzoylchloride, similarly the following compounds were prepared:

E 4-bromobenzamide: m.p 190° C.

F 4-bromo-N-methyl-benzamide: m.p. 169° C.

G 4-bromo-N,N-dimethylbenzamide: 72° C.

H 4-bromo-pyrrolidinylcarbonylbenzene: m.p. 80° C.

EXAMPLE 1

(11β,17α)-11,21-Bis[4-(dimethylamino)phenyl]-17-hydroxy-19-norpregna-4,9-dien-20-yn-3-one a) 27 g (100 mmol) of estra-4,9-diene-3,17-dione, dissolved in 270 ml of tetrahydrofuran (THF) and 270 ml of methanol, were cooled to −10° C. and treated with 2.27 g (60 mmol) of sodium borohydride. The solution was stirred for 30 min at −10° C. Work-up was accomplished by dropwise addition of 8 ml of 50% acetic acid. The mixture was extracted with ethyl acetate, the organic layers were washed with brine, dried on anhydrous magnesium sulfate, filtered and evaporated to dryness resulting in 27.2 g of 17β-hydroxy-estr-4,9-diene-3-one.

b) 25 g of the previously obtained material were dissolved in 375 ml of dichloromethane; 125 ml of ethylene glycol, 75 ml of trimethylorthoformate and 250 mg of p-toluenesulfonic acid were added and the mixture was refluxed for 20 min. After cooling, 200 ml of a saturated sodium hydrogen carbonate solution were added and the resulting mixture was extracted with dichloromethane. Evaporation in vacuo followed by purification of the resulting oil by column chromatography using silicagel, provided 19.9 g of 17α-hydroxy-estra-5(10),9(11)-diene-3-one 3-(cyclic 1,2-ethanediyl acetal) as an oil.

c) 19.9 g (62.9 mmol) of 17α-hydroxy-estra-5(10),9(11)-diene-3-one 3-(cyclic 1,2-ethanediyl acetal) were dissolved in 400 ml of dichloromethane. 27.6 g (336 mmol) of sodium acetate were added followed by 36.2 (168 mmol) of pyridinium chlorochromate and the mixture was stirred at ambient temperature. After 2 hours, 143.5 ml of 2-propanol were added and stirring was continued for 1 hour. The mixture was filtered over celite, evaporated and partitioned between ethyl acetate (1350 ml) and water (675 ml). The organic layer was separated, washed with brine, dried with anhydrous magnesium sulfate and filtered. Evaporation followed by purification by column chromatography using silicagel provided 10.9 g of estra5(10),9(11)-diene-3,17-dione 3-(cyclic 1,2-ethanediyl acetal). Melting point: 152° C.

d) A mixture of 13 g (116.2 mmol) of potassium tert. butoxide, 55 ml of THF and 18.7 ml of tert. butanol was cooled to 0°–5° C. under inert atmosphere. Acetylene was bubbled through the mixture for one hour; then 9.43 g (30 mmol) of estra-5(10),9(11)-diene-3,17-dione 3(cyclic 1,2-ethanediyl acetal), dissolved in 50 ml of THF were added. Stirring was continued for 1.5 hrs at 0°–5° C. under acetylene atmosphere. Work-up was accomplished by pouring the mixture into a saturated aqueous ammonium chloride solution, followed by ethyl acetate extraction. The organic layers were washed with brine, dried with anhydrous magnesium sulfate, filtered and evaporated to give 10.4 g of 17α-ethynyl-17β-hydroxy-estra-5(10),9(11)-diene-3-one 3-(cyclic 1,2ethanediyl acetal).

e) 10 g (29.4 mmol) of 17α-ethynyl-17β-hydroxy-estra-5(10),9(11)-diene-3-one 3-(cyclic 1,2-ethanediyl acetal) were dissolved in 150 ml of dichloromethane. Subsequently 0.91 ml of pyridine, 2.84 ml of trifluoroacetophenone and 18.8 ml of 30% hydrogen peroxide were added and the resulting two-phase system was vigorously stirred at room-temperature for 36 hrs. The mixture was poured into water and the organic layer was washed twice with a saturated sodium thiosulfate solution. Drying with anhydrous magnesium sulfate, filtering and evaporation provided a semi-solid mass consisting of a mixture of epoxides. Trituration with toluene afforded 4.22 g of 5α,10α-epoxy-17α-ethynyl-17β-hydroxy-estr- 9(11)-ene-3-one 3-(cyclic 1,2-ethanediyl acetal).

f) 158 mg of CuCl were added at 0°–5° C. to a solution of p-dimethylaminophenylmagnesium bromide in THF, prepared from 1.49 g of magnesium (61 mmol), 30 ml of THF and 11.8 g (58.9 mmol) of 4-bromo-N,N-dimethylaniline. After stirring for 30 min at 0°–5° C., 4.2 g of 5α,10α-epoxy-17α-ethynyl-17β-hydroxy-estr-9(11)-ene-3-one   3-(cyclic 1,2-ethanediyl acetal) in 42 ml of THF were added dropwise. After being stirred for 2.5 hrs at ambient temperature, the solution was poured into a saturated ammonium chloride solution and extracted with ethyl acetate. The organic layers were washed until neutral, dried with anhydrous magnesium sulfate, filtered and evaporated in vacuo and the residue was chromatographed using silicagel. This provided after crystallization from ether/heptane 3.2 g of pure 5α,17β-dihydroxy-11β-[4-(N,N-dimethylamino)phenyl]-17α-ethynyl-estr-9-ene-3-one 3-(cyclic 1,2-ethanediyl acetal). Melting point: 198° C.

g) 3.0 g (6.3 mmol) of 5α,17β-dihydroxy-11β-[4-(N,N-dimethylamino)phenyl]-17α-ethynyl-estr-9-ene-3-one (cyclic 1,2-ethanediyl acetal) were dissolved in 39 ml of pyrrolidine. Subsequently 1.26 g of 4-bromo-N,N-dimethylaniline (6.3 mmol), 33 mg of palladium(II) acetate, 33 mg of copper(I) iodide and 99 mg of triphenylphosphine were added and the mixture was refluxed for one hour under inert atmosphere. After cooling, the mixture was poured into a 50% aqueous ammonium chloride solution and extracted with ethyl acetate. The organic layers were washed with brine, dried with anhydrous magnesium sulfate, filtered and evaporated to dryness, yielding a crystalline mass. Trituration with diethyl ether provided 2.45 g of pure 11,21-bis[(dimethylamino)-phenyl]-5α,17β-dihydroxy-pregn-9-ene-20-yn-3-one 3-(cyclic 1,2-ethanediyl acetal). Melting point: 150° C.

h) 2.45 g (4.0 mmol) of 11,21-bis[(dimethylamino)phenyl]-5α,17β-dihydroxy-pregn-9-ene-20-yn-3-one 3-(cyclic 1,2-ethanediyl acetal) were dissolved in 123 ml of acetone and with stirring 4.9 ml of 6N $H_2SO_4$ were added. After stirring for 30 min at ambient temperature, the mixture was neutralized with sodium hydrogen carbonate, followed by extraction with ethyl acetate. The organic layer was washed until neutral, dried with anhydrous magnesium sulfate, filtered and evaporated in vacuo. The residue was purified by column chromatography using silicagel. This afforded 1.2 g of pure (11β,17α)-11,21-bis[4-(dimethylamino)phenyl]-17-hydroxy-19-norpregna-4,9-dien-20-yn-3-one. $[α]^{20}_D=-12°$ (C=1, chloroform).

EXAMPLE 2

3E- and 3Z-(11β,17α)-11,21-bis[4-(dimethylamino)phenyl]-17-hydroxy-19-norpregna-4,9-dien-20-yn-3-one oxime 1.0 g (1.9 mmol) of the product obtained under example 1 h were dissolved in 5 ml pyridine. 660 mg (9.5 mmol) of hydroxylamine hydrochloride were added and the mixture was stirred at room temperature for 30 min. The mixture was poured into water, neutralized with dilute hydrochloric acid and extracted with ethyl acetate. The organic layers were dried with anhydrous magnesium sulfate, filtered and evaporated to dryness. The crude oxime was subjected to chromatographic separation using silicagel, which resulted in 550 mg of (3E,11β,17α)-11,21-bis[4-(dimethylamino)phenyl]-17-hydroxy-19-norpregna-4,9-dien-20-yn-3-one oxime, having a specific rotation of $[α]^{20}_D=-19°$ (c=0.5, dioxane) and 230 mg of (3Z,11β,17α)-11,21-bis[4-(dimethylamino)phenyl]-17-hydroxy-19-norpregna-4,9-dien-20-yn-3-one oxime, having a specific rotation of $[α]^{20}_D=-9°$ (c=0.5, dioxane).

EXAMPLE 3

3α- and 3β-(11β,17α)-11,21-di[4-(dimethylamino)phenyl]-19-norpregna-4,9-dien-20-yne-3,17-diol A solution of 1.26 g (5 mmol) of lithium tri(tert-butoxy)aluminum hydride in 7 ml dry THF was added to an ice-cold solution of 1.07 g (2 mmol) of the product obtained under example 1 h. Stirring was continued for two hours. The mixture was poured into water, slightly acidified with 50% acetic acid and extracted with dichloromethane. Evaporation of the organic layers gave 1.35 g of a mixture of the 3α- and 3β-hydroxysteroid. Separation by column chromatography using silicagel provided 180 mg of pure (3β,11β,17α)-11,21-bis[4-(dimethylamino)phenyl]-19-norpregna-4,9-dien-20-yne-3,17-diol, having a specific rotation of $[α]^{20}_D=-32°$ (c=0.5, dioxane) and 110 mg of pure (3α,11β,17α)-11,21-bis[4-(dimethylamino)phenyl]-19-norpregna-4,9- dien-20-yne-3,17-diol, having a specific rotation of $[α]^{20}_D=-111°$ (c=0.5, dioxane).

EXAMPLE 4

The following products were prepared from 5α,17β-dihydroxy-11β-[4-(N,N-dimethylamino)phenyl]-17α-ethynyl-estr-9-ene-3-one 3-(cyclic 1,2-ethanediyl acetal) (see example 1f) by using the appropriate starting material for the Heck coupling reaction (according to the procedure of example 1g), followed by the acidic dehydration and deprotection as described in example 1h:

A using 4-bromo-(1-pyrrolidinyl)benzene the reaction resulted in (11β,17α)-11-[4-(dimethylamino)phenyl]-17-hydroxy- 21-[4-(1-pyrrolidinyl)phenyl]-19-norpregna-4,9-dien-20-yn-3-one having a specific rotation of $[α]^{20}_D=-19°$ (c=1, chloroform).

B using 4-bromo-(methylsulfonyl)benzene the reaction resulted in (11β,17α)-11-[4-(dimethylamino)phenyl]-17-hydroxy-21-[4-(methylsulfonyl)phenyl]-19-norpregna-4,9-dien-20-yn-3-one having a specific rotation of $[α]^{20}_D=-23°$ (c=0.5, dioxane).

C using 4-bromo-(methylsulfinyl)benzene the reaction resulted in (11β,17α)-11-[4-(dimethylamino)phenyl]-17-hydroxy-21-[4-(methylsulfinyl)phenyl]-19-norpregna-4,9-dien-20-yn-3-one; melting point: 175° C.

D using 4-bromophenylsulfonamide the reaction resulted in 4-[(11β,17α)-11-[4-(dimethylamino)phenyl]-17-hydroxy-3-oxo-19-norpregna-4,9-dien-20-yn-21-yl]benzenesulfonamide; $[α]^{20}_D=-26°$ (c=0.5, dioxane).

E using 4-bromo-N-methylphenylsulfonamide the reaction resulted in 4-[(11β,17α)-11-[4-(dimethylamino)phenyl]-17-hydroxy-3-oxo-19-norpregna-4,9-dien- 20-yn-21-yl]-N-methyl-benzenesulphonamide; $[\alpha]^{20}_D = -30°$ (c=0.5, dioxane).

F using 4-bromo-N,N-dimethylphenylsulfonamide the reaction resulted in 4-[(11β,17α)-11-[4-(dimethylamino)phenyl]-17-hydroxy-3-oxo-19-norpregna-4,9-dien-20-yn-21yl]-N,N-dimethylbenzenesulfonamide; $[\alpha]^{20}_D = -34°$ (c=0.5, dioxane).

G using 4-bromo-pyrrolidinylsulfonylbenzene the reaction resulted in [(11β,17α)-11-[4-(dimethylamino)phenyl]-17-hydroxy-21-[4-(1-pyrrolidinylsulfonyl)phenyl]-19-norpregna-4,9-dien-20-yn-3-one; $[\alpha]^{20}_D = -37°$ (c=0.5, dioxane).

H using 4-bromobenzamide the reaction resulted in 4-[(11β,17α)-11-[4-(dimethylamino)phenyl]-17-hydroxy-3-oxo-19-norpregna-4,9-dien-20-yn-21-yl]benzamide; $[\alpha]^{20}_D = -28°$ (c=0.5, dioxane).

I using 4-bromo-pyrrolidinylcarbonylbenzene the reaction resulted in (11β,17α)-11-[4-(dimethylamino)phenyl]-17-hydroxy-21-[4-(1-pyrrolidinylcarbonyl)phenyl]-19-norpregna-4,9-dien-20-yn-3-one; $[\alpha]^{20}_D = -30°$ (c=0.5, dioxane).

J using 4-bromo-N,N-dimethylbenzamide the reaction resulted in 4-[(11β,17α)-11-[4-(dimethylamino)phenyl]-17-hydroxy-3-oxo-19-norpregna-4,9-dien-20-yn-21-yl]-N,N-dimethylbenzamide; $[\alpha]^{20}_D = -26°$ (c=0.5, dioxane).

K using 4-bromo-N-methylbenzamide the reaction resulted in 4-[(11β,17α)-11-[4-(dimethylamino)phenyl]-17-hydroxy-3-oxo-19-norpregna-4,9-dien-20-yn-21-yl]-N-methylbenzamide; $[\alpha]^{20}_D = -30°$ (c=0.5, dioxane).

L using N-[(4-bromo)phenyl]-2-pyrrolidinone the reaction resulted in 1-[4-[(11β,17α)-11-[4-(dimethylamino)phenyl]-17-hydroxy-3-oxo-19-norpregna-4,9-dien-20-yn-21-yl]phenyl]-2-pyrrolidinone; $[\alpha]^{20}_D = -32°$ (c=0.5, dioxane).

M using 4-[(trifluoromethyl)sulfonyl]oxy-2-methyl-(methylsulfonyl)benzene the reaction resulted in (11β,17α)-11-[4-(dimethylamino)phenyl]-17-hydroxy-21-[3-methyl-4-(methylsulfonyl)phenyl]-19-norpregna-4,9-dien-20-yn-3-one having a specific rotation of $[\alpha]^{20}_D = -30°$ (C=0.5, dioxane).

N using 4-bromo-(ethylsulfonyl)benzene (Example II) the reaction resulted in (11β,17α)-11-[4-(dimethylamino)phenyl]-21-[4-(ethylsulfonyl)phenyl]-17-hydroxy-19-norpregna-4,9-dien-20-yn-3-one having a specific rotation of $[\alpha]^{20}_D = -28.6°$ (C=0.5, dioxane).

O using 4-bromo-(isopropylsulfonyl)benzene (Example II) the reaction resulted in (11β,17α)-11-[4-(dimethylamino)phenyl]-17-hydroxy-21-[4-(isopropylsulfonyl)phenyl]-19-norpregna-4,9-dien-20-yn-3-one having a specific rotation of $[\alpha]^{20}_D = -30.8°$ (C=0.5, dioxane).

P using 4-bromo-(cyclopentylsulfonyl)benzene (Example II) the reaction resulted in (11β,17α)-21-[4-(cyclopentylsulfonyl)phenyl]-11-[4-(dimethylamino)phenyl]-17-hydroxy-19-norpregna-4,9-dien-20-yn-3-one having a specific rotation of $[\alpha]^{20}_D = -31.8°$ (C=0.5, dioxane).

Q using 4-bromo-(fluoromethylsulfonyl)benzene [prepared according to the procedure described in J. Org. Chem. 58, 2791, (1993); $^1$H NMR (200 MHz, CDCl$_3$: 5.13 ppm, doublet 2H, $^1J_{H,F}=47$ Hz; $^{19}$F NMR (188 MHZ, CDCl$_3$: -211.7 ppm)]the reaction resulted in (11β,17α)-11-[4(dimethylamino)phenyl]-21-[4-(fluoromethylsulfonyl)phenyl]-17-hydroxy-19-norpregna-4,9-dien-20-yn-3-one having a specific rotation of $[\alpha]^{20}_D = -20.8°$ (C=0.5, dioxane).

R using 4-bromo-(difluoromethylsulfonyl)benzene (C.A. 80, 70488r, 1974)) the reaction resulted in (11β,17α)-21-[4-(difluoromethylsulfonyl)phenyl]-11-[4-(dimethylamino)phenyl]-17-hydroxy-19-norpregna-4,9-dien-20-yn-3-one having a specific rotation of $[\alpha]^{20}_D = -29.8°$ (C=0.5, dioxane).

S using 4-bromo-(trifluoromethylsulfonyl)benzene [J. Org. Chem. 25, 60 (1960)]the reaction resulted in (11β,17α)-11-[4-(dimethylamino)phenyl]-17-hydroxy-21-[4-(trifluoromethylsulfonyl)phenyl]-19-norpregna-4,9-dien-20-yn-3-one having a specific rotation of $[\alpha]^{20}_D = -32°$ (C=0.5, dioxane).

EXAMPLE 5

According to the procedure described in example 1f, the Cu-catalyzed Grignard reaction of phenylmagnesium bromide with 5α,10α-epoxy-17α-ethynyl-17β-hydroxy-estra-9(11)-ene-3-one 3-(cyclic 1,2-ethanediyl acetal), provided 5α,17β-dihydroxy-17α-ethynyl-11β-phenyl-estr-9-ene-3-one 3-(cyclic 1,2-ethanediyl acetal). Melting point: 187° C.

The following products were prepared from 5α,17β-dihydroxy-17α-ethynyl-11β-phenyl-estr-9-ene-3-one 3-(cyclic 1,2-ethanediyl acetal) by using the appropriate starting material for the Heck coupling reaction (according to the procedure of example 1g), followed by the acidic dehydration and deprotection as described in example 1h:

A using 4-bromo-N,N,-dimethylaniline the reaction resulted in (11β,17α)-21-[4-(dimethylamino)phenyl]-17-hydroxy-11-phenyl-19-norpregna-4,9-dien-20-yn-3-one having a specific rotation of $[\alpha]^{20}_D = -83°$ (c=0.5, dioxane).

B using 4-bromo-(methylsulfonyl)benzene the reaction resulted in (11β,17α)-17-hydroxy-21-[4-(methylsulfonyl)phenyl]-11-phenyl-19-norpregna-4,9-dien-20-yn-3-one having a specific rotation of $[\alpha]^{20}_D = -71°$ (c=0.5, dioxane).

EXAMPLE 6

According to the procedure described in example 1f, the Cu-catalyzed Grignard reaction of 3,4-methylenedioxophenylmagnesium bromide with 5α,10α-epoxy-17α-ethynyl-17β-hydroxy-estr-9(11)-ene-3-one 3-(cyclic 1,2ethanediyl acetal) provided 5α,17β-dihydroxy-17α-ethynyl-11β-(1,3-benzodioxol-5-yl)-estr-9-ene-3-one 3-(cyclic 1,2-ethanediyl acetal). Melting point: 155° C.

The following products have been prepared from 5α,17β-dihydroxy-17α-ethynyl-11β-(1,3-benzodioxol-5-yl)-estr-9-ene-3-one 3-(cyclic 1,2-ethanediyl acetal) by using the appropriate starting material for the Heck coupling reaction (according to the procedure of example 1g), followed by the acidic dehydration and deprotection as described in example 1h:

A using 4-bromo-N,N,-dimethylaniline the reaction resulted in (11β,17α)-11-(1,3-benzodioxol-5-yl)-21-[4-

(dimethylamino)phenyl]-17-hydroxy-19-norpregna-4, 9-dien-20-yn-3-one; [α]20D=-63° (c=1, chloroform).

B using 4-bromo-methylsulfonylbenzene the reaction resulted in (11β,17α)-11-(1,3-benzodioxol-5-yl)-21-[4-(methylsulfonyl)phenyl]-17-hydroxy-19-norpregna-4, 9-dien-20-yn-3-one; melting point 228°–229° C.

C using N-(4-bromophenyl)-2-pyrrolidinone (Example III) the reaction resulted in 1-[4-[(11β,17α)-11-(1,3-benzodioxol-5-yl)-17-hydroxy-3-oxo-19-norpregna-4, 9-dien-20 yn-21-yl)phenyl]-2-pyrrolidinone; $[α]^{20}_D$=−72° (C=1, dioxane).

D using 4-bromo-(cyclopentylsulfonyl)benzene the reactions resulted in (11β,17α)-11-(1,3-benzodioxol-5-yl)-21-[4-(cyclopentylsulfonyl)phenyl]-17-hydroxy-19-norpregna-4,9-dien-20-yn-3-one; $[α]^{20}_D$=−61.2° (C=0.5, dioxane).

EXAMPLE 7

According to the procedure described in example 1f, the Cu-catalyzed Grignard reaction of 4-fluorophenyl-magnesium bromide with 5α,10α-epoxy-17α-ethynyl-17β-hydroxy-estr-9(11)-ene-3-one 3-(cyclic 1,2-ethanediyl acetal) provided 5α,17β-dihydroxy-17α-ethynyl-11β-(4-fluorophenyl)-estr-9-ene-3-one 3-(cyclic 1,2-ethanediyl acetal).

The following products were prepared from 5α,17β-dihydroxy-17α-ethynyl-11β-(4-fluorophenyl)-estr-9-ene-3-one 3-(cyclic 1,2-ethanediyl acetal) by using the appropriate starting material for the Heck coupling reaction (according to the procedure of example 1g), followed by the acidic dehydration and deprotection as described in example 1h:

A using 4-bromo-(methylsulfonyl)benzene, the reaction resulted in (11β,17α)-11-(4-fluorophenyl)-17-hydroxy-21-[4-(methylsulfonyl)phenyl]-19-norpregna-4, 9-dien-20-yn-3-one; melting point: 256° C.

B using N-(4-bromophenyl)-2-pyrrolidinone, the reaction resulted in 1-[4-[(11β,17α)-11-(4-fluorophenyl)-17-hydroxy-3-oxo-19-norpregna-4,9-dien-20-yn-21-yl]phenyl]-2-pyrrolidinone; melting point: 166° C.

C using 4-bromopyrrolidinylsulfonylbenzene the reaction resulted in (11β,17α)-11-(4-fluorophenyl)-17-hydroxy-21-[4-(1-pyrrolidinylsulfonyl)phenyl]-19-norpregna-4,9-dien-20-yn-3-one; $[α]^{20}_D$=−68° (c=0.5, dioxane).

D using 4-bromo-N,N-dimethylaniline the reaction resulted in (11β,17α)-11-[α-fluorophenyl]-17-hydroxy-21-[4-(dimethylamino)phenyl]-19-norpregna-4, 9-dien-20-yn-3-one; $[α]^{20}_D$=−92° (c=0.5, dioxane).

EXAMPLE 8

According to the procedure described in example 1f, the Cu-catalyzed Grignard reaction of 3,4-ethylenedioxophenylmagnesium bromide with 5α,10α-epoxy-17-α-ethynyl-17β-hydroxy-estr-9(11)-ene-3-one 3-(cyclic 1,2-ethanediyl acetal) provided 5α,17β-dihydroxy-17α-ethynyl-11β-(2,3-dihydro-1,4-benzodioxin-6-yl)estr-9-ene-3-one 3-(cyclic 1,2-ethanediyl acetal). Melting point: 253° C. (dec.).

The following products have been prepared from 5α,17β-dihydroxy-17α-ethynyl-11β-(2,3-dihydro-1,4-benzodioxin-6-yl)estr-9-ene-3-one 3-(cyclic 1,2-ethanediyl acetal) by using the appropriate starting material for the Heck coupling reaction (according to the procedure of example 1g), followed by the acidic dehydration and deprotection as described in example 1h:

A using N-(4-bromophenyl)-2-pyrrolidinone the reaction resulted in 1-[4-[(11β,17α)-11-(2,3-dihydro-1,4-benzodioxin-6-yl)-17-hydroxy-3-oxo-19-nor-pregna-4,9-dien-20-yn-21-yl)phenyl]-2 pyrrolidinone; $[α]^{20}_D$=−55° (C=0.5, dioxane).

B using 4-bromo-(methylsulfonyl) benzene the reaction resulted in (11β,17α)-11-(2,3-dihydro-1,4-benzodioxin-6yl)-17-hydroxy-21-[4-(methylsulfonyl) phenyl]-19-norpregna-4,9-dien-20-yn-3-one; $[α]^{20}_D$=−47° (C=0.5, dioxane).

C using 4-bromo-(methylsulfinyl)benzene the reaction resulted in (11β,17α)-11-(2,3-dihydro-1,4-benzodioxin-6-yl)-17-hydroxy-21-[4-(methylsulfinyl)phenyl]-19-norpregna-4,9-dien-20-yn-3-one; $[α]^{20}_D$=−47° (C=0.5, dioxane).

EXAMPLE 9

(11β,17α)-11-(2,2-difluoro-1,3-benzodioxol-5-yl)-21-[4-(methylsulfonyl)-phenyl]-17-hydroxy-19-norpregna-4,9-dien-20-yn-3-one According to the procedure described in example 1f, the Cu-catalyzed Grignard reaction of 3,4-(difluoromethylenedioxo)phenylmagnesium bromide [see J. Org. Chem. 37, 673 (1972)] with 5α,10α-epoxy-17α-ethynyl-17β-hydroxy-estr-9(11)-ene-3-one 3-(cyclic 1,2-ethanediyl acetal) provided 11β-(2,2-difluoro-1,3-benzodioxol-5-yl)-5α,17β-dihydroxy-17α-ethynyl-estr-9-ene-3-one 3-(cyclic 1,2-ethanediyl acetal).

The Heck coupling reaction of 11β-(2,2-difluoro-1,3-benzodioxol-5-yl)-5α,17β-dihydroxy-17α-ethynyl-estr-9-ene-3-one 3-(cyclic 1,2-ethanediyl acetal) with 4-bromo-(methylsulfonyl)benzene according to the procedure described in example 1g followed by acidic dehydration and deprotection as described in example 1h resulted in (11β, 17α)-11-(2,2-difluoro-1,3-benzodioxol-5-yl)-21-[4-(methylsulfonyl)phenyl]-17-hydroxy-19-norpregna-4,9-dien-20-yn-3-one, that was crystallized from ethanol.

Melting point: 275° C.

We claim:

1. A 11,21-bisphenyl-19-norpregnane derivative of the formula

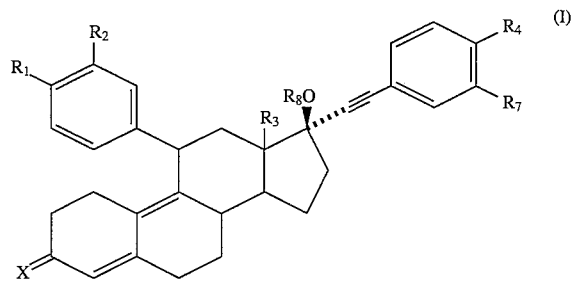

wherein $R_1$ is selected from H, halogen, (1–6C)alkoxy, and $NR_5R_6$, $R_5$ and $R_6$ being independently hydrogen or (1–6C)alkyl or $R_5$ and $R_6$ together being (3–6C)alkylene;

$R_2$ is hydrogen; or $R_1$ and $R_2$ together are a (1–3C)alkylenedioxy group that is unsubstituted or substituted by at least one halogen atom;

$R_3$ is methyl or ethyl;

$R_4$ is selected from C(O)—$NR_5R_6$, a $SO_n$-(1–6C)alkyl that is unsubstituted or substituted by at least one halogen atom, $SO_n$-(3–6C) cycloalkyl, $SO_2$—$NR_5R_6$, 2-oxypyrrolidinyl, and $NR_5R_6$;

n is 1 or 2;

$R_7$ is H or (1–6C)alkyl;

$R_8$ is H or carboxy-1-oxo(1–6C)alkyl; and

X is selected from (H,OH), O, and NOH;

or a pharmaceutically acceptable salt thereof.

2. The 11,21-bisphenyl-19-norpregnane derivative of claim 1, wherein $R_3$ is methyl and $R_4$ is selected from a $SO_2$-(1–6C)alkyl that is unsubstituted or substituted by at least one fluorine atom, $SO_2$-(3–6C)cycloalkyl, and $NR_5R_6$.

3. The 11,21-bisphenyl-19-norpregnane derivative of claim 1, wherein $R_4$ is $N(CH_3)_2$ or $SO_2CH_3$.

4. The 11,21-bisphenyl-19-norpregnane derivative of claim 1, wherein $R_1$ is $N(CH_3)_2$, and $R_2$ is hydrogen; or $R_1$ and $R_2$ form together a methylenedioxy group.

5. The 11,21-bisphenyl-19-norpregnane derivative of claim 1, wherein the derivative is (11β,17α)-11-[4-(dimethylamino)phenyl]-17-hydroxy-21-[4-methylsulfonyl)phenyl]-19-norpregna-4,9-dien-20-yn-3-one.

6. A method of preparing the 11,12-bisphenyl-19-norpregnane derivative of claim 1 comprising dehydrating and deprotecting a compound of formula II

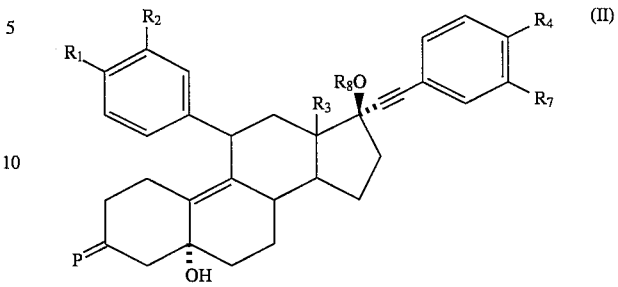

wherein P is a protected keto-group, and, optionally converting the product into the corresponding 3-hydroxy- or 3-oxime derivative, after which the compound obtained is optionally converted into a pharmaceutically acceptable salt.

7. A pharmaceutical composition comprising an effective amount of the 11,21-bisphenyl-19-norpregnane derivative of claim 1 for anti-glucocorticoid activity and pharmaceutically suitable auxiliaries.

8. A method for treating glucocorticoid dependent diseases in a patient comprising administering to the patient an effective amount of the 11,21-bisphenyl-19-norpregnane derivative of claim 1 for effecting anti-glucocorticoid activity.

* * * * *